(12) United States Patent
D'Armiento et al.

US011565004B2

(10) Patent No.: US 11,565,004 B2
(45) Date of Patent: Jan. 31, 2023

(54) IN VIVO IMAGING OF MATRIX METALLOPROTEINASES IN LUNG DISEASE

(71) Applicant: The Trustees of Columbia University in the City of New York, New York, NY (US)

(72) Inventors: Jeanine D'Armiento, New York, NY (US); Lynne Johnson, New York, NY (US); Monica Goldklang, Demarest, NJ (US); Yared Tekabe, Bronx, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 805 days.

(21) Appl. No.: 16/303,599

(22) PCT Filed: May 19, 2017

(86) PCT No.: PCT/US2017/033600
§ 371 (c)(1),
(2) Date: Nov. 20, 2018

(87) PCT Pub. No.: WO2017/201441
PCT Pub. Date: Nov. 23, 2017

(65) Prior Publication Data
US 2021/0008231 A1    Jan. 14, 2021

Related U.S. Application Data

(60) Provisional application No. 62/339,598, filed on May 20, 2016.

(51) Int. Cl.
*A61K 51/04* (2006.01)
*C07B 59/00* (2006.01)
(52) U.S. Cl.
CPC ........ *A61K 51/0455* (2013.01); *C07B 59/002* (2013.01)
(58) Field of Classification Search
CPC ............................... A61K 51/04; C07B 59/00
See application file for complete search history.

(56) References Cited

PUBLICATIONS

Reza Golestani ety al, Matrix Metalloproteinase-Targeted Imaging of Lung Inflammation and Remodeling, J Nucl Med, 58, 138-143. (Year: 2017).*
H.R. Wiltshire et al., The synthesis of labelled forms of cipemastat, J. Labelled Cpd, Radiopharm, 44, 149-164, (Year: 2001).*
Klaus Kopka et al., Synthesis and preliminary biological evaluation of new radioiodinated MMP inhibitors for imaging MMP activity in vivo, Nucl Med and Biol, 31, 257-267. (Year: 2204).*
A. Madani et al., Quantitative computed tomography assessment of lung structure and function in pulmonary emphysema, Eur Respir J, 18, 720-730. (Year: 2001).*
Yan Cai et al. Noninvasive Monitoring of Pulmonary Fibrosis by Targeting Matrix Metalloproteinases (MMPs), Molecular Pharmaceutics, 10, 2237-2247. (Year: 2013).*
Schafers, M. et al., "Scintigraphic Imaging of Matrix Metalloproteinase Activity in the Arterial Wall In Vivo", Circulation, Mar. 11, 2004.
International Search Report dated Aug. 22, 2017 in connection with PCT International Application No. PCT/US2017/033,600.
Written Opinion of the International Searching Authority dated Aug. 22, 2017 in connection with PCT International Application No. PCT/US2017/033,600.
Fei, X. et al., "Synthesis of Radiolabeled Biphenylsulfonamide Matrix Metalloproteinase Inhibitors as New Potential PET Cancer Imaging Agents", Bioorganic and Medicinal Chemistry Letters, Nov. 27, 2002.
Ouchi, H. et al., "The role of collagenases in experimental pulmonary fibrosis", Pulrnonery Pharmacology and Therapeutics, Oct. 27, 2007.

* cited by examiner

*Primary Examiner* — Michael G. Hartley
*Assistant Examiner* — Jagadishwar R Samala
(74) *Attorney, Agent, or Firm* — Gary J. Gershik

(57) ABSTRACT

The present invention provides a method of imaging a subject's lung which comprises contacting the subject's lung with a matrix metalloproteinase inhibitor labeled with a radioisotope under conditions such that the inhibitor binds to matrix metalloproteinase in the lung, and then imaging the radiolabeled inhibitor bound to matrix metalloproteinase in the subject's lung.
The invention also provides Ro 32-3555 labeled with a radioisotope.

4 Claims, 9 Drawing Sheets

IN VIVO IMAGING OF MATRIX METALLOPROTEINASES IN LUNG DISEASE

This application is a § 371 national stage of PCT International Application No. PCT/US2017/033600, filed May 19, 2017 and claims the benefit of U.S. Provisional Application No. 62/339,598, filed May 20, 2016, the contents of each of which are hereby incorporated by reference.

Throughout this application, various publications are referenced. Full citations for these references are present immediately before the claims. The disclosures of these publications in their entireties are hereby incorporated by reference into this application to more fully describe the state of the art to which this invention pertains.

BACKGROUND OF THE INVENTION

Proteases capable of digesting both collagen and elastin are secreted from inflammatory cells within the lungs of patients with chronic obstructive pulmonary disease (COPD); in addition, epithelial cells are known to produce collagenolytic enzymes (Imai 2001). The initiation and sustaining mechanism of destruction is multi-factorial and diverse from case to case, however connective tissue degradation. is a common, unique and definite mechanism in emphysema development. Multiple MMPs have been implicated in the development of emphysema, including MMP-1, MMP-9, MMP-12, and MMP-13 (Goldklang 2013). MMP-1, a collagenase, is specifically expressed in lung epithelial cells and cigarette smoke directly induces MMP-1 in epithelial cells (Imai 2001, Foronjy 2003, Mercer 2009). An additional collagenase, MMP-13, is also increased in the epithelial cells and macrophages of patients with COPD (Lee 2009).

Due to the importance of metalloproteinase expression in the pathogenesis of a number of diseases radiolabeled metalloproteinase inhibitors have been developed for tumor imaging and for cardiovascular applications (Wagner 2009, Kopka 2004). The uptake of a $^{99m}$Tc-labeled MMP inhibitor (RP805) was reported in atheroma of ApoE null mice (Tekabe 2010). All of the MMP inhibitors studied to date are broad based and were developed for the treatment of inflammatory and degenerative diseases. One of these drugs is a nonpeptidyl broad-spectrum MMP inhibitor CGS27023A with high affinities against MMPs-1, -2, -3, -7, -9, -12, and -13 (Kopka 2004, Faust 2009, Romero-Perez 2009, Ouchi 2008, Rao 2006).

SUMMARY OF THE INVENTION

The present invention provides a method of imaging a subject's long which comprises contacting the subject's lung with a matrix metalloproteinase inhibitor labeled with a radioisotope under conditions such that the inhibitor binds to matrix metalloproteinase in the lung, and then imaging the radiolabeled inhibitor bound to matrix metalloproteinase in the subject's lung.

The invention also provides Ro 32-3555 labeled with a radioisotope.

DETAILED DESCRIPTION OF THE INVENTION

Figure 1:
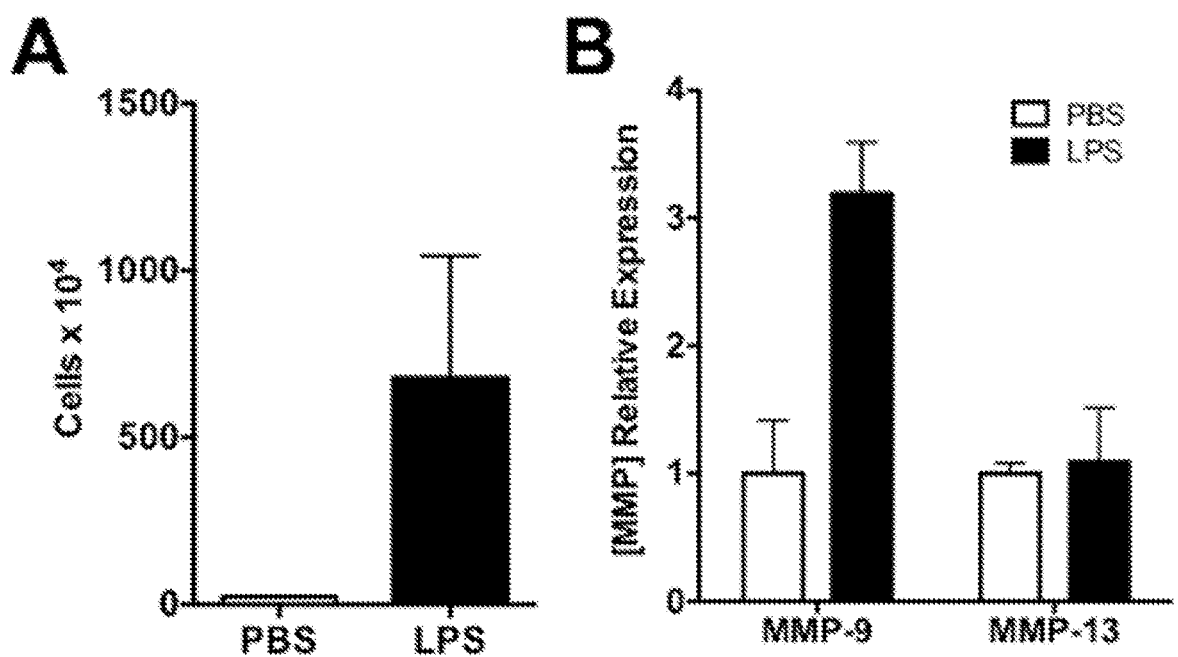
FIG. 1. Increased inflammation and MMP-9 expression in LPS exposed lungs. (A) Increased total BAL (bronchoalveolar lavage fluid) cell count. (B) Increased MMP-9 but not MMP-13 in LPS treated lungs.

The present invention provides a method of imaging a subject's lung which comprises contacting the subject's lung with a matrix metalloproteinase inhibitor labeled with a radioisotope under conditions such that the inhibitor binds to matrix metalloproteinase in the lung, and then imaging the radiolabeled inhibitor bound to matrix metalloproteinase in the subject's lung.

In one embodiment, the matrix metalloproteinase inhibitor is Ro 32-3555 or a modified form of CGS27023A.

In some embodiments, the label is I-123.

In one embodiment, the matrix metalloproteinase inhibitor is Ro 32-3555. In another embodiment, the matrix metalloproteinase inhibitor is a modified form of CGS27023A.

In an embodiment, the modified form of CG527023A has the structure:

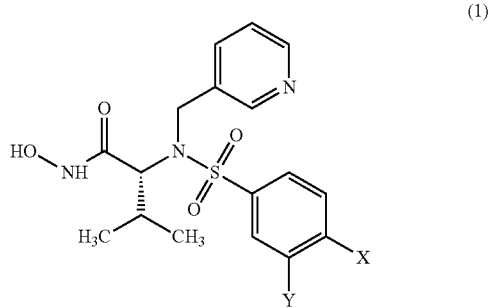

(1)

wherein X is OH and Y is H.

In another embodiment, The the matrix metalloproteinase inhibitor labeled with a radioisotope has the structure:

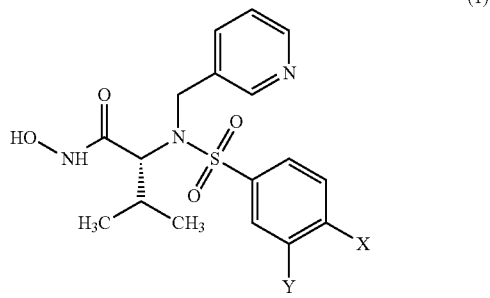

(1)

wherein X is OH and Y is 1-123.

In some embodiments, the subject is suspected of being afflicted with a destructive lung disease. In other embodiments, the subject is afflicted with a destructive lung disease.

The destructive lung disease may be chronic obstructive pulmonary disease (COPD), lymphangioleiomyomatosis (LAM), idiopathic pulmonary fibrosis (IPF), or acute lung injury (ALI) The destructive lung disease may also be emphysema.

In some embodiments, the imaging is single-photon emission computed tomography (SPECT) imaging.

In one embodiment, the method further comprises administering to the subject an amount of the matrix metalloproteinase inhibitor labeled with a radioisotope.

In some embodiments, the method further comprises imaging the subject's lung with a single-photon emission computed tomography (SPECT) scanner. In another embodiment, the method further comprises imaging the subject's lung with a computed tomography (CT) scanner.

In some embodiments, the method further comprises imaging the subject's lung with a SPECT/CT scanner. In one embodiment, the SPECT/CT scanner is a nano-SPECT/CT scanner.

In one embodiment, the method further comprises determining the amount of matrix metalloproteinase (MMP) expression in the lung of the subject.

In some embodiments, the MMP expression is selected from one or more of the group consisting of MMP-1 expression, MMP-9 expression, MMP-12 expression, and MMP-13 expression.

In one embodiment, the method further comprises determining the amount of the label in the lung of the subject.

In some embodiments, the method further comprises determining if the subject is afflicted with destructive lung disease. In another embodiment, the method further comprises determining the degree of lung destruction in the subject.

In an embodiment, the presence of MMP expression in the subject's lung in an amount that is higher than a reference amount indicates that the subject is afflicted with a destructive lung disease.

In one embodiment, the reference amount is based on the amount of MMP expression in a healthy subject's lung.

In another embodiment, the presence of the label in the subject's lung in an amount that is higher than a reference amount indicates that the subject is afflicted with a destructive lung disease.

In one embodiment, the reference amount is based on the amount of the label in a healthy subject's lung.

In some embodiments, the amount of MMP expression present in the subject's lung determines the degree of lung destruction in the subject.

In one embodiment, the amount of the label present in the subject's lung determines the degree of lung destruction in the subject.

The invention also provides Ro 32-3555 labeled with a radioisotope.

In some embodiments, the radioisotope is I-123.

All combinations and subcombinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

The present invention allows the detection of MMPs in vivo and provides a marker of disease activity. The methods allow one to (1) detect the disease at an early stage compared to available imaging techniques and pulmonary function testing and (2) target a relatively specific pathway with molecular lung imaging to directly visualize a process critical to disease initiation and progression.

The experiments herein support the detection of MMP production in vivo utilizing newly developed MMP inhibitor probes. The time point in which these pathways are activated following injury are defined and the imaging studies with structural and physiological changes observed in emphysema may be correlated. In vivo animal models are used to develop the MMP-inhibitor for SPECT-CT imaging and quantify the difference between an MMP signal in the smoke exposed lung and in the normal lung. A novel imaging modality to view lung destructive activity in vivo is established. The up regulation of MMP expression in transgenic models of emphysema is correlated with MMP expression.

in animals exposed to cigarette smoke. The chosen MMP imaging agent, CGS27023A, functions as a competitive inhibitor of multiple MMPs. However, CGS27023A has been modified with a hydroxylation step to be suitable for radioactive iodination, increasing the feasibility of in vivo imaging.

EXAMPLE 1

Preliminary Studies

In Vivo MMP Imaging Following IPS Treatment

PBS (phosphate-buffered saline) control and LPS (lipopolysaccharide) treated C57Bl/6J mice were imaged for MMPs 24 hours after a single dose of intranasal LPS from *Escherichia coli* 0111:B4 (Sigma, 1.5 mg/kg in sterile PBS) to demonstrate support for in vivo SPECT-CT Imaging. Two PBS treated mice and three LPS mice were imaged. This model induces very robust inflammation (FIG. 1A) and induction of MMP-9 but not MHP-13 (FIG. 1B).

In Vivo MNP Imaging

Figure 2:
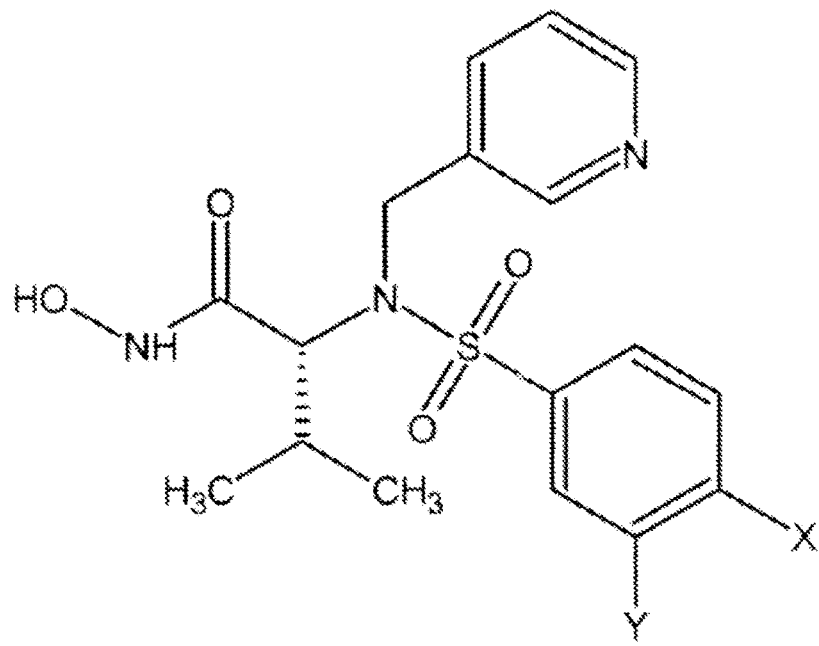
FIG. 2. Structure of CGS27023A and its derivative(s). (a) When X is MeO and Y is H the compound is in its non-derivative form, CGS27023A; (b) when X is OH and Y is H the compound is "CGS27023A with hydroxylation" or "HO-CGS27023A", in which an —OH group is present at point X.
Figure 3:
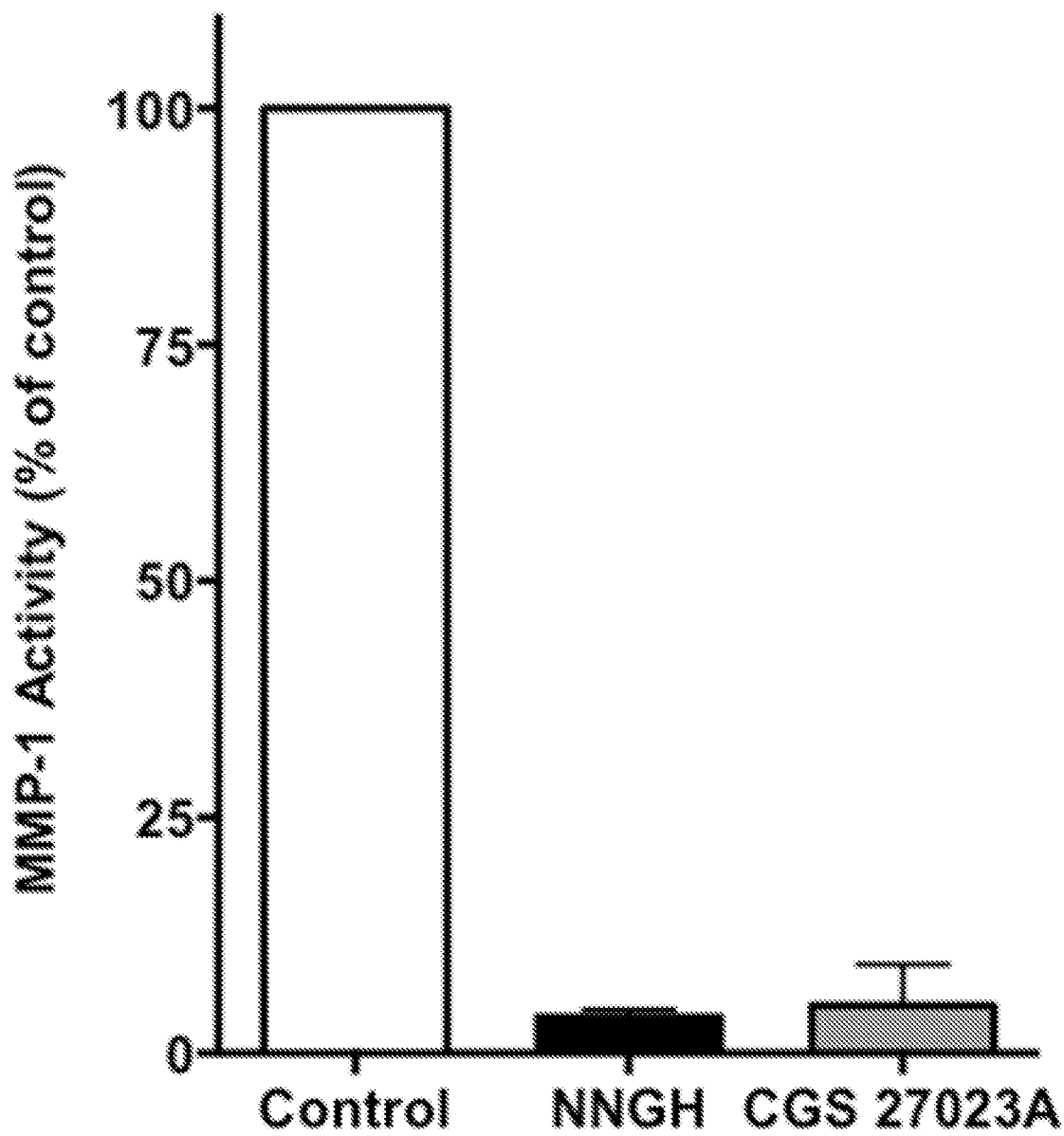
FIG. 3. MMP-1 inhibition by HO-CGS27023A. EnzoLifeSciences, MMP-1 drug discovery kit and inhibitors (N-Isobutyl-N-(4-methoxyphenylsulfonyl) glycyl hydroxamic acid (NNGH) or HO-CGS27023A) were incubated at 37° C. for 30-60 minutes to allow inhibitor-enzyme reaction. After, fluorogenic substrate was added to detect MMP-1 activity. Data are presented as mean+SD. NNGH is a MMP inhibitor.

Direct radio-iodination is used to label the relevant molecules with a gamma emitting radiotracer because of the small size of the molecules (Kopka 2004). An F-18 label for PET imaging may also be used (Behrends 2015). CGS27023A, which has the structure shown in FIG. 2(a), was modified by adding an hydroxyl group and radiolabeled to obtain HO-[$^{123}$I]I-CGS27023A (CGS/$^{123}$I) non-peptidyl hydroxamic acid as a radioligand for assessing MMP activity in vivo with SPECT imaging as previously reported (Kopka 2004). The chemical structure of HO-CGS27023A showing where the hydroxyl group was substituted is shown in. FIG. 2(b). Assays with this compound confirm that it is still a potent inhibitor of collagenase activity after this hydroxylation step (FIG. 3).

Direct iodination with I-123 was performed according to the protocol as described in Markwell 1978. Briefly, the compound was dissolved in DMSO and PBS and carrier free Na $^{123}$I was added to the solution. (800 µCi of Na $^{123}$I per 100 µg protein). The reaction was allowed to proceed for 15 min and the reaction vessel was removed to terminate the iodine oxidation. Doses of approximately 40 µCi CGS/$^{123}$I were drawn and injected into LPS or PBS treated mice.

Figure 4:
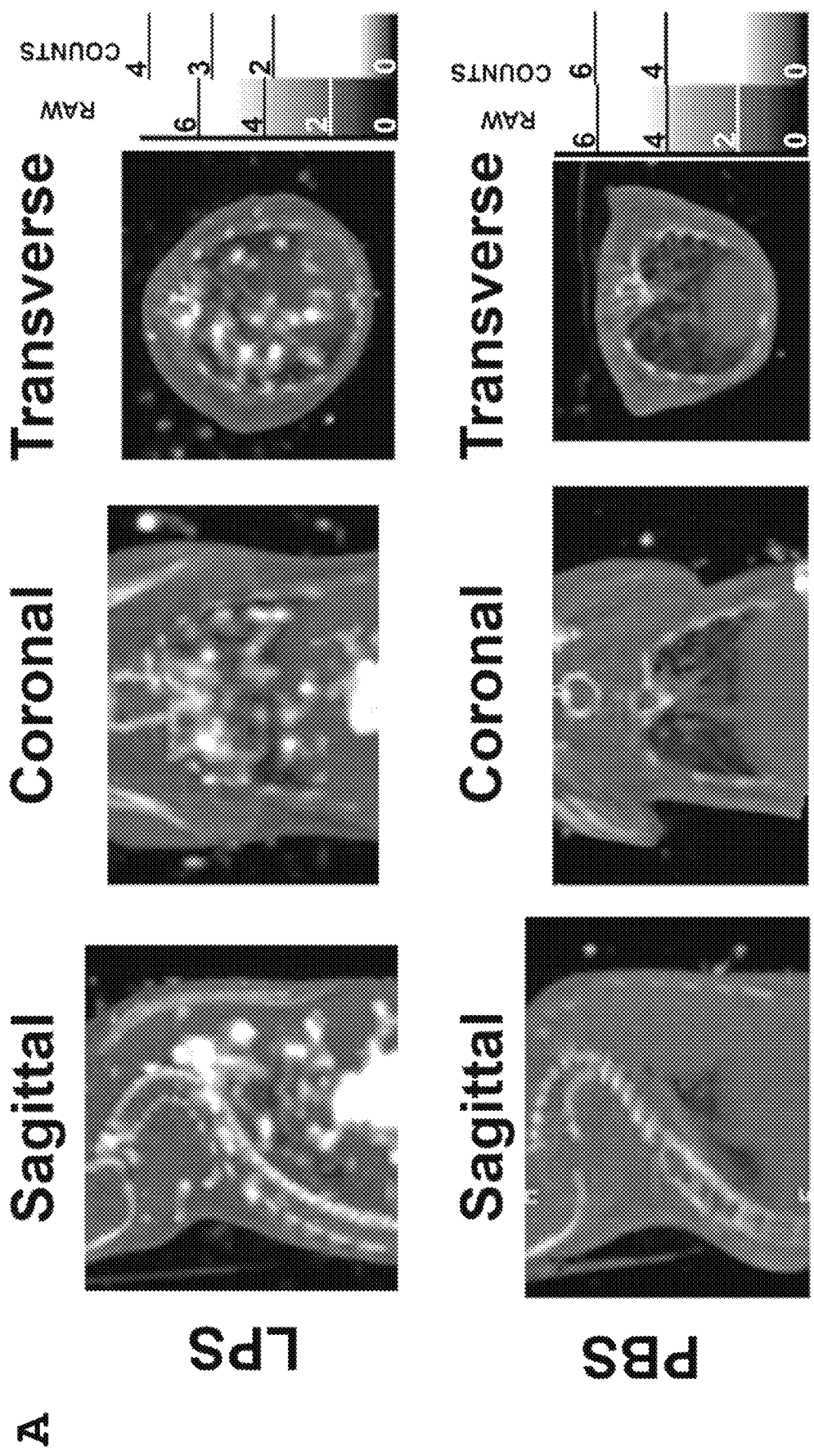
FIG. 4. In vivo CGS/$^{123}$I imaging after intranasal LPS exposure shows abundant MMP uptake. (A) Sagittal, corona, and transverse projections from merged SPECT/CT scans for a mouse exposed to LPS on top and one exposed to PBS (control) on bottom. Tracer uptake is shown and the scale bars are displayed on the right. There is uptake of tracer observed in both lung fields of the LPS exposed mouse and no observable uptake in the PBS exposed mouse. (B) Average (+SD) of 3 LPS and 2 PBS exposed mice with tracer uptake for both lungs quantified as % ID in the graph on the left and uptake in the excised lungs (% ID/g) on the right.
Figure 4:
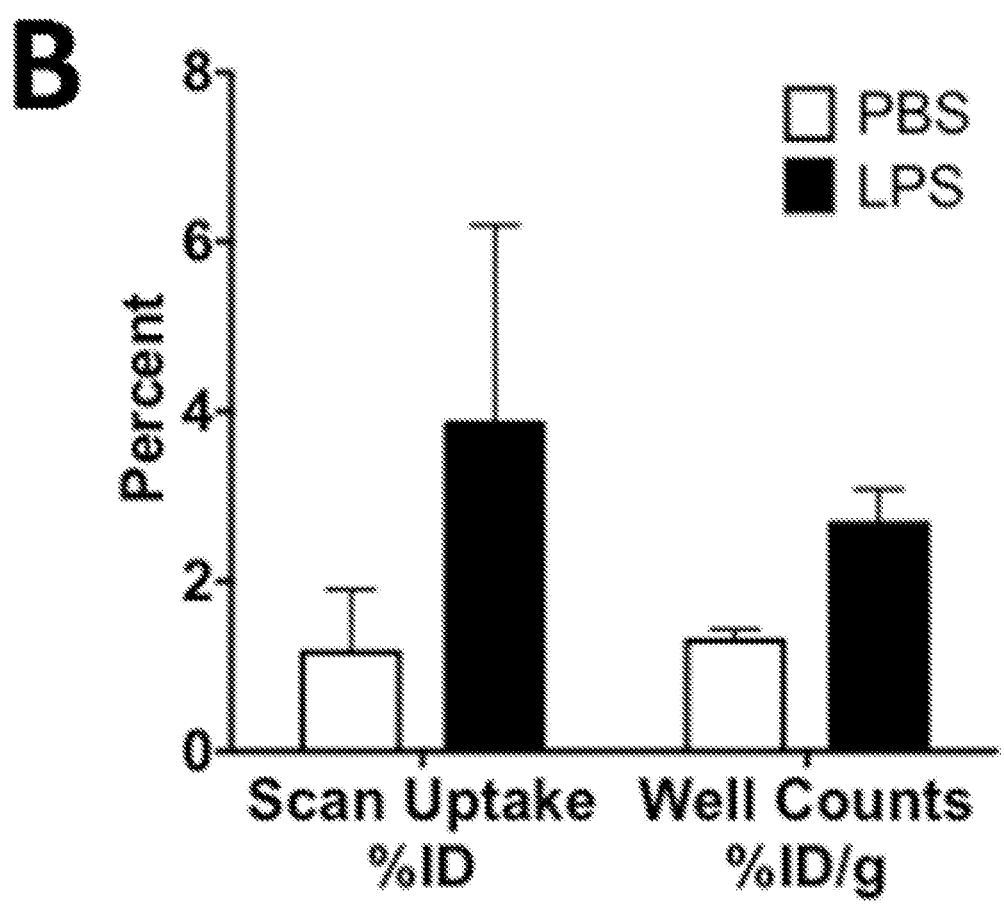

Approximately one hour after femoral vein catheter placement and injection, mice underwent SPECT/CT scanning on a Bioscan nano-SPECT/CT (Mediso). At completion of scanning the mice were euthanized and lung tissue was taken tar gamma well counting. The scan data was reconstructed and regions of interest were drawn around lung activity and uptake of probe measured in MBg (mCi) and divided by decay corrected injected dose (ID) to % ID. The lung tissue was weighed. and counted in the gamma well counter for % ID/g tracer uptake. FIG. 4 shows the results from these experiments. Based on visual assessment of the scans, there was small uptake in the thyroid gland and kidney uptake but no appreciable liver or heart uptake was observed.

These experiments demonstrate that one can synthesize the modified CGS27023A compound and successfully directly iodinate with I-123 and that once synthesized, this compound has an energy profile and half-life favorable for SPECT imaging.

EXAMPLE 2

The imaging studies of this example further demonstrate the clinical value of developing modified CGS27023A (HO-[$^{123}$I]-CGS27023A, radioiodinated non-peptidyl hydroxamic acid) as a radioligand for assessing MMP lung activity. Utilizing both mouse smoke exposure models and the human MMP-1 emphysema transgenic mouse (D'Armiento 1992), SPECT/CT imaging was performed on 3 groups of mace. (WT room air exposed, WT smoke exposed, and MMP-1 transgenic mice).

Direct iodination of modified CGS27023A (specifically, HO-CGS27023A) with I-123 was performed according to Markwell 1978. This iodinated modified. CGS27023A formed is referred to herein as CGS/$^{123}$I. Briefly, the compound was dissolved in DMSO and PBS and added to pre-coated iodination tube. Carrier free Na $^{123}$I was added to the solution (800 µCi of Na$^{123}$I per 100 µg protein). The reaction was allowed to proceed for 15 min and the reaction vessel was removed to terminate the iodine oxidation.

Figure 5:
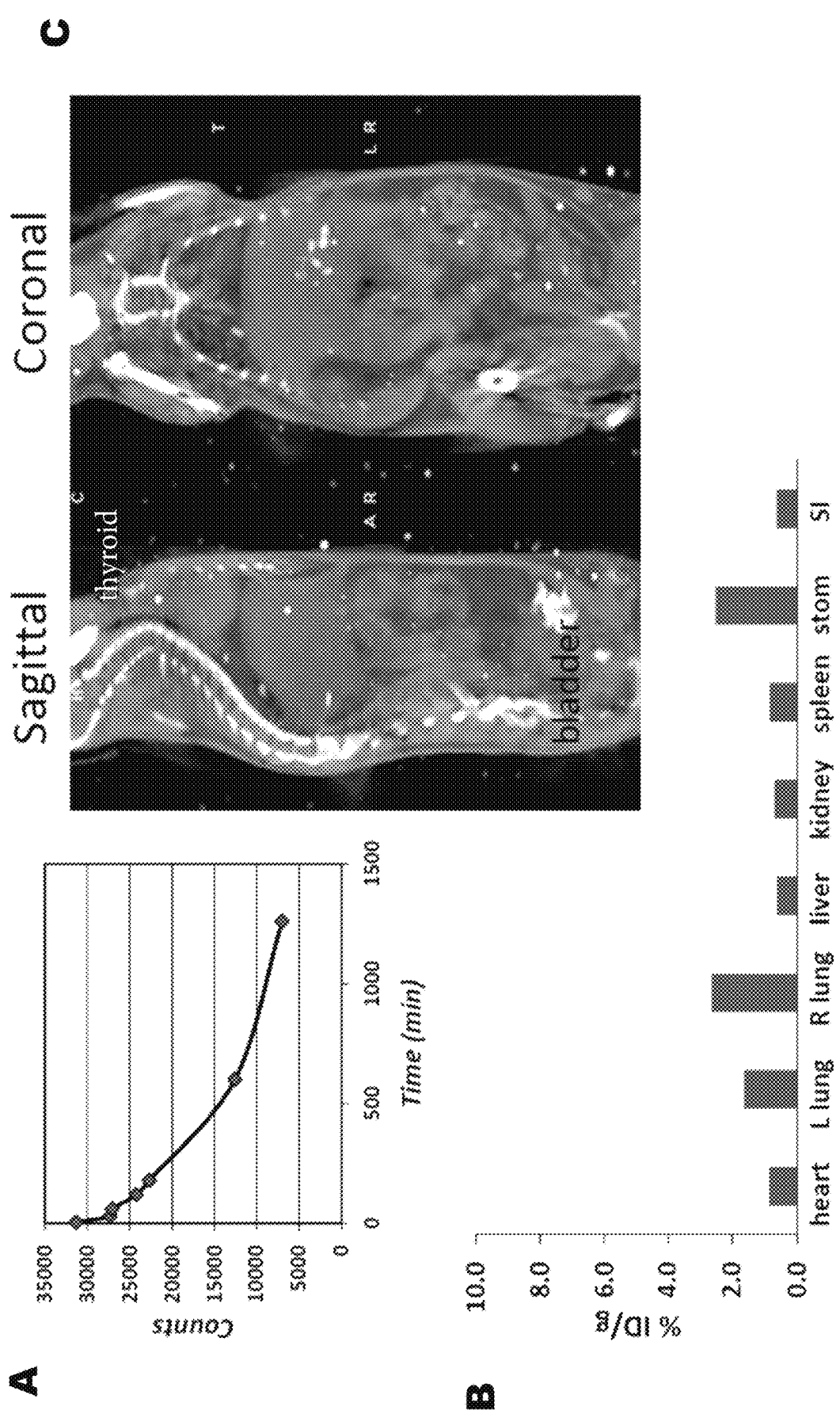
FIG. 5. Blood pool clearance and biodistribution of CGS/$^{123}$I. (A) Blood pool clearance shows optimal imaging timing of 8 hours following injection (B) Organ biodistribution 8 hours after injection of radiotracer in WT mice shows very low tracer uptake in lungs and liver. (C) Full body scans in 2 views of WT mouse injected with CGS/$^{123}$I and imaged at 8 hours. Sagittal image (left) shows bladder and thyroid uptake; coronal images (right) show thyroid uptake but little uptake in other organs.

Doses of approximately 0.150 mCi CGS/$^{123}$I were drawn and injected via a femoral vein catheter and mice were imaged on average 8 hours later. Initially 3 WT mice and 3 TG mice were injected with probe and blood samples taken via tail vein nicking for counting and blood pool clearance determination. The blood pool clearance data showed biexponential washout with $t_{1/2}$ of first component=34 minutes and for the second component=760 minutes (FIG. 5(A)). Optimal imaging time determined from these curves was at approximately 8 hours after injection. Three additional WT mice underwent analysis for radiotracer biodistribution at 8 hours after injection, which showed very low tracer uptake in lungs and liver (FIG. 5(B)). Full body scans in 2 views of WT mouse injected with CGS/$^{123}$I and imaged at 8 hours showed that excretion appears to be mainly via the kidneys at this time point based upon bladder activity. Without pre-administration of a thyroid blocking drug, it was expected to see thyroid uptake of a radioiodinated probe.

Imaging of Smoke Exposed and MMP-1 Transgenic Mice

Figure 6:
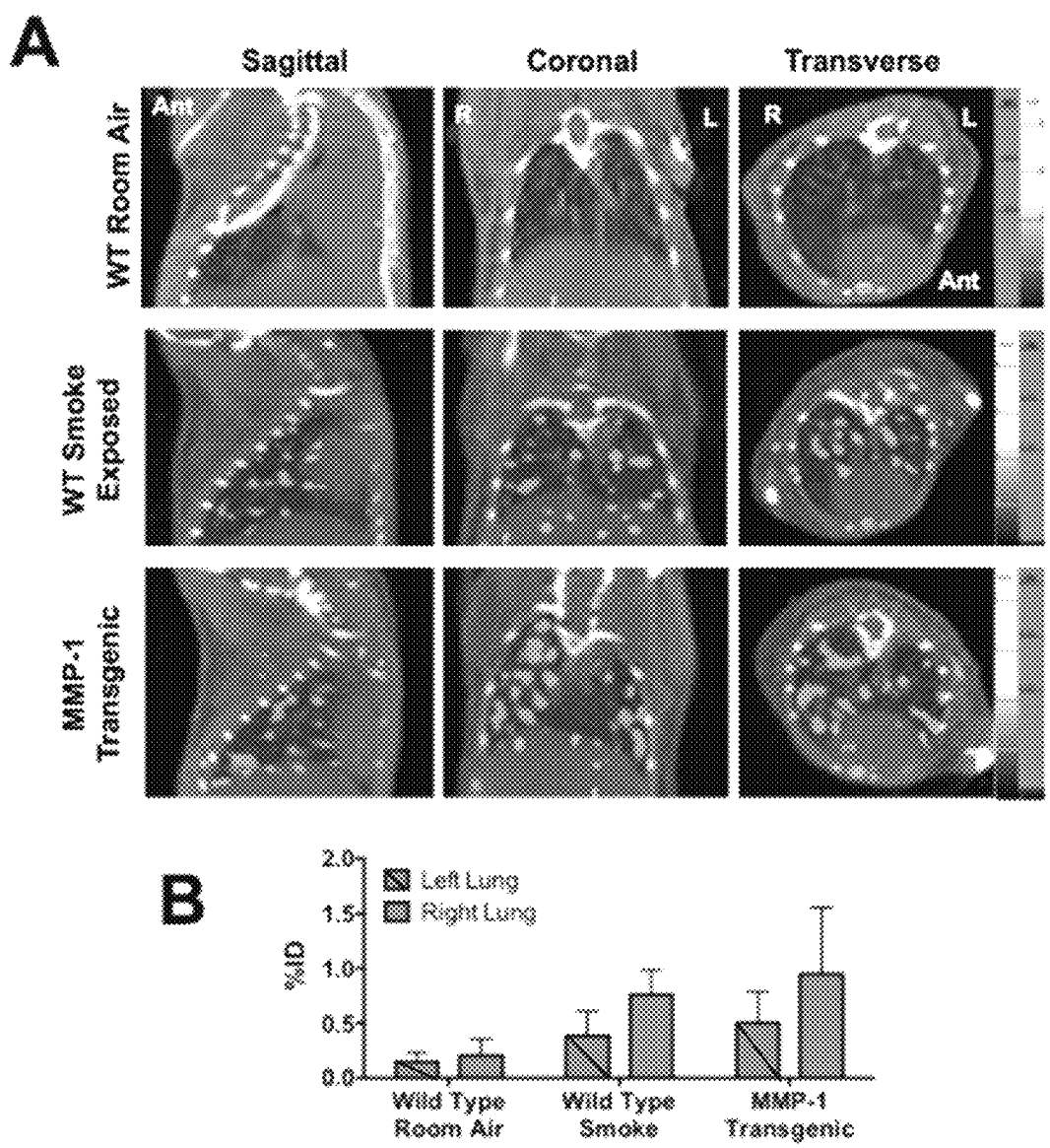
FIG. 6. Increased CGS/$^{123}$I uptake in the lungs of smoke exposed and MMP-1 transgenic mice but not air exposed non-transgenic mice. (A) Representative images from wild-type room air control, wild-type smoke exposed and MMP-1 transgenic mice. (B) Quantitative lung uptake of CGS/$^{123}$I. There is increased uptake in the MMP-1 transgenic and a trend for increased uptake in smoke exposed wild-type mice as compared to control. Mean+SD, n=5 per group.

Following biodistribution and blood pool clearance studies, imaging was performed on MMP-1 transgenic mice, mice that underwent 10 days of smoke exposure, and room air control mice. The MMP-1 transgenic mouse imaged, line 50, is well described to have MMP-1 expression and activity within the lung, and develops emphysema spontaneously, in the absence of smoke or other inflammatory stimuli (D'Armiento 1992). Utilizing the Teague Enterprises Smoke Exposure System, mice were exposed five hours per day, five days per week, for two weeks to cigarette smoke (3R4F University of Kentucky Research Cigarettes) with a total particulate matter maintained at approximately 100 mg/m$^3$. Littermate room air wild-type mice served as a control. The scan data was reconstructed with regions of interest drawn around lung activity and uptake of probe measured in MBq (mCi) and divided by decay corrected injected dose (ID) to yield % ID. The lung tissue was weighed and counted in the well counter for % ID/g tracer uptake. Examples of scans from the 3 groups of mice are provided in FIG. 6. There is little or no uptake in the lungs of the room air exposed WT mouse while the smoke exposed WT mouse and the transgenic mouse show good lung uptake.

Figure 7:
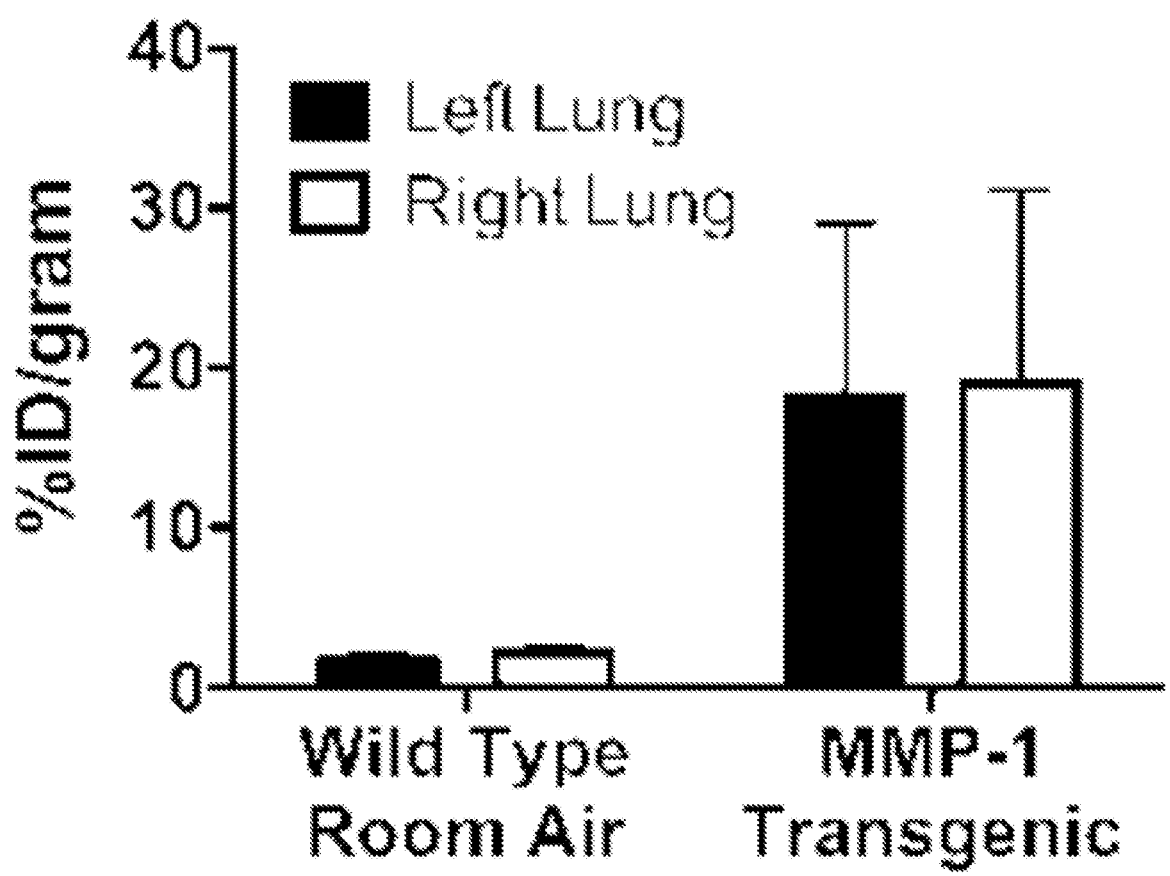
FIG. 7. Gamma well counts in the MMP-1 transgenic mice. Mean+SD, p=0.08 for right lungs and p=0.06 for left lungs, n=3 per group.

Quantification shows that uptake was significantly higher in the lungs of MMP-1 transgenic as compared to WT room air control mice (p=0.03 for both right and left lungs), and there was a trend to a significant increase when comparing WT room air control mice to smoke exposed WT mice (right lung p=0.006, left lung p=0.07). Gamma well counting for MMP-1 transgenic mice and litter mate wild-type control showed a trend toward an increased % ID/g tissue, primarily due to small sample size and large variance in the MMP-1 transgenic values (FIG. 7).

These results show favorable parameters for CGS/$^{123}$I as a probe to image expression of MMPs in diseased lungs. I-123 is used routinely in clinical nuclear medicine studies. The half-life of I-123 of 13 hours allows time for blood pool clearance and has little uptake in normal lungs, or in the liver overlapping with the lower lobes. Probe uptake was increased in the MMP transgenic mice and during cigarette smoke exposure in these preliminary experiments. This data supports the other examples set forth in this application. It has been demonstrated that not only is it possible to detect MMPs under inflammatory conditions, but it is also possible to detect specific single MMP expression in a transgenic mouse without additional injury.

EXAMPLE 3

Radioiodination of Ro 32-3555

The structure and chemical name of Ro 32-3555 (Cat. No. 2916) is below.

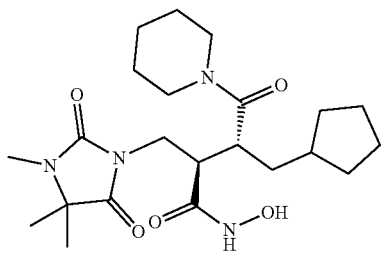 [SMILES: CN1C(=O)N(C[C@H](C(=O)NO)[C@@H](CC2CCCC2)C(=O)N2CCCCC2)C(=O)C1(C)C]

(αR, βR) -β-(Cyclopentylmethyl)-N-hydroxy-γ-oxo-α-[(3,4,4-trimethyl-2,5-dioxo-1-imidazolidinyl)methyl.]-1-piperidinebutanamide The compound Ro 32-3555 is linked with Bolton-Hunter Reagent (Sulfo-SHPP) to introduce tyrosine-like residues for subsequent iodination. The conjugated compound is then radiolabeled with $^{123}$I using the indirect method of Chizzonite. Briefly, Tris Iodination buffer is added to pre-coated Pierce iodination Tubes. Carrier free Na $^{123}$I is added to the solution. The activated iodide is added to the solution and mixed and reacted for 6-9 min at room temperature. Scavenging buffer is added and the reaction mixture is incubated for additional 5 min. After addition of Tris/BSA to the solution, the iodinated solution is passed through a chromatography column. One cc sample is eluted from the column. Fractions containing the tracer are pooled and QC performed.

EXAMPLE 4

The procedures of Example 1 and Example 2 are performed, except that CGS/$^{123}$I is replaced by radiolabeled Ro 32-3555 (described in Example 3).

Radiolabeled Po 32-3555 demonstrates similar biodistribution shown by CGS/[123]I. Additionally, radiolabeled Ro 32-3555 is shown to have an energy profile and half-life favorable for SPECT imaging.

In the experiment having 3 groups of mice (WT room air exposed, WT smoke exposed, and MMP-1 transgenic mice) described in Example 2, SPECT/CT imaging shows similar results for mice administered radiolabeled Ro 32-3555 as those administered CGS/[123]I. Thus, radiolabeled Ro 32-3555, like CGS/[123]i, may be used to detect specific single MMP expression in a transgenic mouse without additional injury.

EXAMPLE 5

CGS/[123]I Radiotracer for In Vivo Imaging

In this example, the rapid blood pool clearance is confirmed and biodistribution in mice is completed.

Blood Pool Clearance, Biodistribution and Imaging

CGS/$^{123}$I is prepared as outlined in Example 1 above. Blood pool clearance and biodistribution studies are performed for CGS/$^{123}$I using 10 C57Bl/6J mice. A dose of approximately 40 microcuries (μCi) CGS/[123]I (100 μL) is injected through a femoral vein catheter. Thereafter a small droplet of blood (about 10-20 μL) is obtained by tail vein nicking at 2, 5, 10, 15, 30, 60, 120, and 180 minutes. At 10, 30, 60, and 120 minutes, each mouse undergoes planar imaging in the anteroposterior position for a preset time of 10 minutes. At 180 minutes, mice undergo SPECT/CT imaging (Bioscan nanoSPECT/CT).

Image Analysis

The SPECT/CT scans are reconstructed and processed using VicoQuant software (Invicro, Boston, Mass.). Regions of interest (ROIs) are drawn around each lung on serial 10 voxel thick transverse sections from apex to base, excluding the very basal segments in which up-scatter from below the diaphragm such as liver is seen. Activity for each transverse section for both right and left lungs are summed for each lung and expressed as mCi using a calibration factor. Total tracer uptake in mCi for each lung is divided by the decay corrected injected dose to yield the % injected dose (% ID). The animals are sacrificed, the lungs are removed and tissues are counted in the gamma well counter for % ID/gram of tissue.

EXAMPLE 6

The Use of CGS/[123]I Identifies MMP Activity in MMP-1 and MMP-9 Transgenic Mice The ability of CGS/$^{123}$I to detect MMP expression in established transgenic mouse models is tested. Two animal models, which express different MMPs in different cell types, are utilized. The first MMP-1 transgenic develops emphysema after aging due to MMP-1 expression in the epithelial cells of the lung (D'Armjento 1992, Foronjy 2003).

Figure 8:
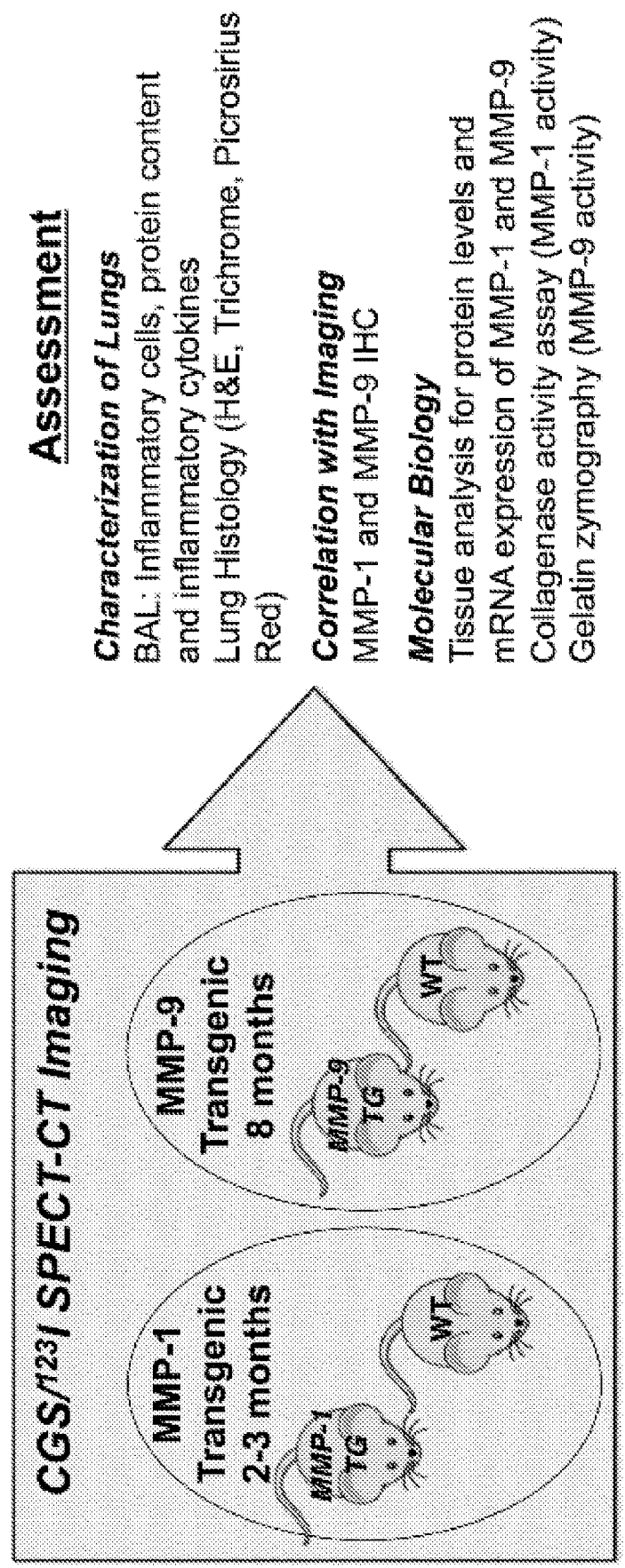
FIG. 8. Experimental groups and design for MMP-targeted imaging of MMP-1 and MMP-9 transgenic mice. 10 mice per group are imaged.

This model is ideal because mice do not have an ortholog of human MMP-1 (Carver 2015), which means that the littermate controls should not have any MMP expression (D'Armiento 1992). The second model expresses MMP-9 in the macrophages of the lung, which increases upon injury (Foronjy 2008, Mehra 2010). The experimental plan is outlined in FIG. 8. MMP-1 and MMP-9 transgenic mice and their litter mate wild-type controls undergo CGS/$^{123}$I SPECT-CT imaging with a full assessment of MMP expression and activity following sacrifice. Ten (10) mice are analyzed per group.

EXAMPLE 7

Imaging of an In Viva COPD Exacerbation Model with Increased MMP-13 Expression

It is well accepted that viral infections have significant consequences in smokers, particularly in patients with chronic obstructive pulmonary disease (COPD) and can cause severe disease exacerbations with loss of lung function (Wedzicha 2013, Donaldson 2002) and increased mortality (Gelbert 1990). MMP-13 levels were examined in an in vivo model system of acute viral exacerbations of COPD (Fang 2008). After two weeks of smoke exposure (Teague Enterprises Smoke Exposure System, 3R4F University of Kentucky Research Cigarettes, total particulate matter maintained at approximately 100 mg/m$^3$), mice were anesthetized with isoflurane, and PR8 influenza virus administered by nasal aspiration. A dose of 0.05 LD50 in C57Bl/6 was administered in 50 µl aliquots (Kang 2008). After an additional period of up to two weeks, mice were sacrificed, bronchoalveolar lavage was performed and tissue analyzed. For morphometric analysis, 20 pictures at 10× magnification were taken and destructive index calculated.

Figure 9:
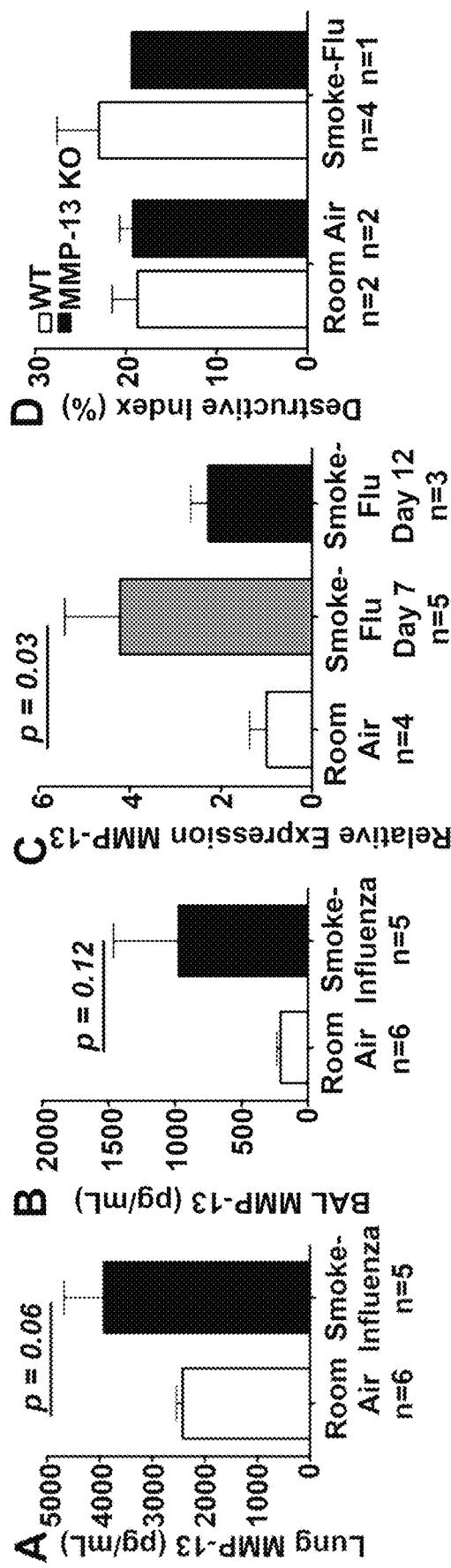
FIG. 9: Increased MMP-13 in the setting of smoke exposure and influenza virus infection. Increased MMP-13 protein levels in the lungs (A) and BAL fluid (B) of smoke exposed and influenza infected mice (sacrificed day 15 post-infection). (C) MMP-13 expression peaks at day 7 following influenza infection, and expression then decreases further out from injury. (D) Increased lung destruction in smoke exposed and influenza infected mice (sacrificed day 15 post-infection). Data are presented as mean+S. E. M.

In this model, increased levels of MMP-13 protein (MMP-13 ELISA kit, Cloud-Clone Corp., Houston, Tex.) in whole lung homogenates were found (FIG. 9(A)) and bronchoalveolar fluid (FIG. 9(B)) at the terminal end point (day 15 after influenza infection) was found. MMP-13 RNA expression showed MMP-13 levels peaking at 7 days following influenza infection, and declining at subsequent examination on day 12 (FIG. 9(C)).

Figure 10:
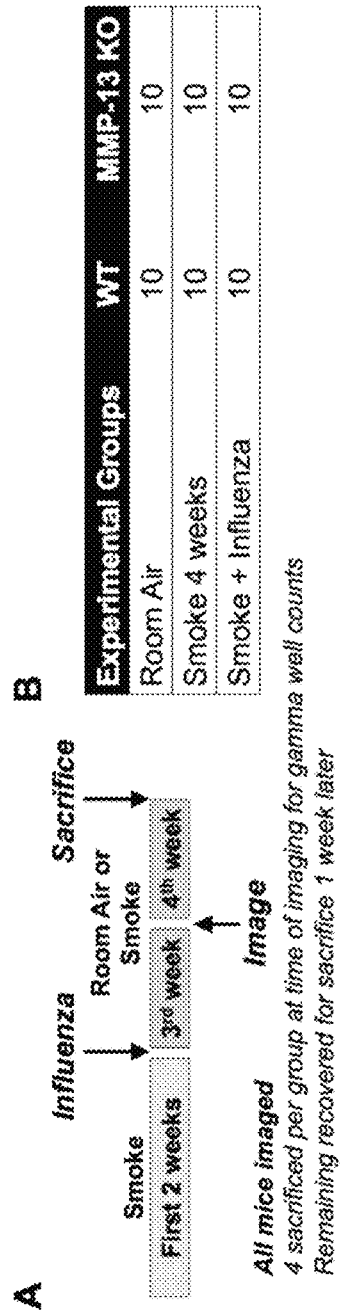
FIG. 10: Groups and design for in vivo MMP imaging in a COPD exacerbation model. (A) Experimental flow. (B) Experimental groups.

Utilizing this smoke-virus model system, imaging as outlined above is undertaken to examine in vivo MMP-13 within the lungs of MMP-13 knockout and wild-type mice. This allows for (1) evaluation of the ability of this imaging probe to detect MMP-13 in a disease relevant animal model and (2) assessment of the specificity of the imaging probe for MMP-13 utilizing a unique MMP-13 knockout mouse (Takaishi 2008). Animal groups and experimental design are outlined in FIG. 10. Animals are imaged at the time of peak MMP-13 expression (day 7), and a subset of animals recovered after imaging for sacrifice at the time of peak destruction (day 15). With this experimental design, not only is the ability of CGS/$^{123}$I to image MMP-13 at peak levels determined, but it is determined if MMP-13 imaging signal can predict the degree of lung destruction at a later time point.

Analysis of Inflammation, MMP Immunohistochemistry, Zymography and Lung Morphometry At the time of sacrifice, the chest is opened and careful neck dissection is performed. A 20-gauge catheter is inserted into the trachea and secured with a silk suture. Bronchoalveolar lavage is performed with 1 mL sterile PBS, and following this, the left lung is removed for gamma well counting. The right lung is pressure perfused with 10% formalin to 25 cm H$_2$O for 20 minutes. Tissues are stored in formalin for at least 24 hours prior to paraffin embedding and sectioning (4 µm). Sections are stained with hematoxylin and eosin (H&E) for histological analysis including morphometry, immunohistochemistry and quantification of inflammatory cells. Immunohistochemistry for MMP-1 (human, in MMP-1 transgenic mouse only), -9, and -13 is performed on at least four sections from each mouse for correlation with imaging results. Morphometric analysis of the H&E stained lungs is performed as outlined above. Quantitative signals from the CGS/$^{123}$I imaging is correlated with measures of MMP expression and activity including immunohistochemistry, gelatin zymography, casein zymbgraphy, and collagenase activity assay. In addition, in particular for the smoke-influenza experiments, the signal of uptake 7 days post infection, the time of peak MMP-13 expression, is correlated with the degree of emphysema at the terminal endpoint.

Number of Mice and Statistical Analysis

For each group of mice, a minimum of 8 mice are analyzed for imaging, the primary end point. An average for each type of measurements is calculated, with the standard deviation. The statistical analysis of the data is performed using the unpaired 2-tailed Student's t-test, with p<0.05 considered significant. An identification of a 10-20% change in radiotracer uptake as a consequence of transgenic MMP expression or smoke and influenza exposure is preferred. In order to have an 80% power to detect a 20% difference in radiotracer uptake, a total of 8 animals is required in each subgroup (Alpha=0.05, 1-Beta=0.2).

Results

The MP-1 and MMP-9 transgenic mice have increased MMP signal on imaging as compared to their wild-type littermate controls (Table 1). In the smoke-influenza model system, wild-type mice have increased signal on imaging compared to baseline. This signal is absent or is reduced in the MMP13 knockout, depending on the potential induction of other MMPs in this model. This model system is able to detect differences between uninjured and injured mice.

TABLE 1

| Signal strength of CGS/$^{123}$I in the MMP transgenic mice. | | |
|---|---|---|
| MMP Signal | Transgenic | Wild-Type |
| MMP-1 TG/WT | + | − |
| MMP-9 TG/WT | + | − |
| MMP-13 KO/WT Smoke Influenza | −/+ | +++ |

If the signal is not robust due to the low expression of MMP-9 in the MMP-9 macrophage mouse, a consequence may be that it takes a year for emphysema to develop in this model (Foronjy 2008). In this case, the animals are induced with an injury (Mehra 2010) increasing MMP-9 levels so as to detect a signal with imaging. An alternative is to perform quantitative studies by crossing the MMP-1 transgenic mice to generate homozygous MMP-1 transgenic mice, which would have double the production of MMP-1 (D'Armiento 1992). The CGS27023A is a broad-spectrum inhibitor, therefore the imaging is not specific to single MMPs.

EXAMPLE 8

The procedures of Examples 5, 6 and 7 are performed, except that CGS/$^{123}$I is replaced by radiolabeled Ro 32-3555 (described in Example 3). The results of radiolabeled Ro 32-3555 are similar to those of CGS/$^{123}$I, however, radiolabel ed Ro 32-3555 is more selective.

REFERENCES

1. Washko G R. Diagnostic imaging in COPD. Semin Respir Crit Care Med. 2010; 31(3):276-85.
2. MacManus M, Everitt S, Hicks R J. The evolving role of molecular imaging in non-small cell lung cancer radiotherapy. Seminars in radiation oncology. 2015; 25(2):133-42.
3. Everitt S, Hicks R J, Ball D, Kron T, Schneider-Koisky M, Walter T, Binns D, Nac Manus M. Imaging cellular proliferation during chemo-radiotherapy: a pilot study of serial 18F-FLT positron emission tomography/computed tomography imaging for non-small-cell lung cancer. International journal of radiation oncology, biology, physics. 2009; 75(4):1098-104.

4. Rischin D, Hicks R J, Fisher R, Binns D, Corry J, Porceddu S, Peters L J, Trans-Tasman Radiation Oncology Group S. Prognostic. significance of [18F]-misonidazole positron emission tomography-detected tumor hypoxia in patients with advanced head and neck cancer randomly assigned to chemoradiation with or without tirapazamine: a substudy of Trans-Tasman Radiation Oncology Group Study 98.02. Journal of clinical oncology: official journal of the American Society of Clinical Oncology. 2006; 24(13):2098-104.
5. Postema E J, McEwan A J, Piauka T A, Kumar P, Richmond D A, Abram D N, Wiebe L I. Initial results of hypoxia imaging using 1-alpha-D: -(5-deoxy-5-[18F]-fluoroarabinofuranosyl)-2-nitroimidazole (18F-FAZA), European journal of nuclear medicine and molecular imaging. 2009; 36(10):1565-73.
6. Nahrendorf M, Frantz S, Swirski F R, Mulder W J, Randolph G, Ertl G, Ntziachristos V, Piek J J, Stroes E S, Schwaiger M, Mann D L, Fayad Z A, Imaging Systemic Inflammatory Networks in Ischemic Heart Disease. Journal of the American College of Cardiology. 2015; 65(15): 1583-91. PMCID: PMC4401833.
7. Jung N H, Lee N H. Molecular imaging in the era of personalized medicine. Journal of pathology and translational medicine. 2015; 49(1):5-12. PLACID: PMC4357402.
8. Pauwels R A, Buist A S, Calverley P M, Jenkins C R, Hurd S S. Global strategy for the diagnosis, management, and prevention of chronic obstructive pulmonary disease. NHLBI/WHO Global Initiative for Chronic Obstructive Lung Disease (GOLD) Workshop summary. Am J Bestir Crit Care Med. 2001; 163(5):1256-76.
9. D'Armiento J, Dalai S S, Okada Y, Berg R A, Chada K. Collagenase expression in the lungs of transgenic mice causes pulmonary emphysema. Cell. 1992; 71(6M955-61.
10. Imai K, Dalai S S, Chen E S, Downey R, Schulman L L, Ginsburg M, D'Armiento J. Human collagenase (matrix metalloproteinase-1) expression in the lungs of patients with emphysema. American journal of respiratory and critical care medicine. 2001; 163(3 Pt 1):786-91.
11. Foronjy R E, Okada Y, Cole R, D'Armiento J. Progressive adult-onset emphysema in transgenic mice expressing human MMP-1 in the lung. American journal of physiology Lung cellular and molecular physiology. 2003; 284(5):L727-37.
12. Mercer B A, Kolesnikova N, Sonett J, D'Armiento J. Extracellular regulated kinase/mitogen activated protein kinase is up-regulated in pulmonary emphysema and mediates matrix metalloproteinase-1 induction by cigarette smoke. J Biol Chem. 2004; 279(17):17690-6.
13. Seagrave J, Barr E B, March T H, Nikula K J. Effects of cigarette smoke exposure and cessation on inflammatory cells and matrix metalloproteinase activity in mice. Exp Lung Res. 2004; 30(1): 1:15.
14. Valenca S S, da Hora K, Castro P, Moraes V G, Carvalho L, Porto L C. Emphysema and metalloelastase expression in mouse lung induced by cigarette smoke. Toxicol Pathol. 2004; 32(3):351-6.
15. Mercer B A, Lemaitre V, Powell C A, D'Armiento J. The Epithelial Cell in Lung Health and Emphysema Pathogenesis. Curr Respir Med Rev. 2006; 2(2):101-42. PMCID: PMC2721228.
16. Egebiad M, Werb Z. New functions for the matrix metalloproteinases in cancer progression. Nature reviews Cancer. 2002; 2(3):161-74.
17. Segura-Valdez L, Pardo A, Gaxiola M, Uhal B D, Becerril C, Selman M. Upregulation of gelatinases A and B, collagenases 1 and 2, and increased parenchymal cell death in COPD. Chest. 2000; 117(3):684-94.
18. Yokohori N, Aoshiba K, Nagai A, Respiratory Failure Research Group in J. Increased levels of cell death and proliferation in alveolar wall cells in patients with pulmonary emphysema. Chest. 2004; 125(2):626-32.
19. Kasahara Y, Tuder R N, Cool C D, Lynch D A, Flores S C, Voelkel N F. Endothelial cell death and decreased expression of vascular endothelial growth factor and vascular endothelial growth factor receptor 2 in emphysema. American journal of respiratory and critical care medicine. 2001; 163(3 Pt 1):737-44.
20. Imai K, Mercer B A, Schulman L L, Sonett J R, D'Armiento J M. Correlation of lung surface area to apoptosis and proliferation in human emphysema. The European respiratory journal. 2005; 25(2):250-8.
21. Foronjy R, Nkyimbeng T, Wallace A, Thankachen J, Okada Y, Lemaitre V, D'Armiento J. Transgenic expression of matrix metalloproteinase-9 causes adult-onset emphysema in mice associated with the loss of alveolar elastin. American journal of physiology Lung cellular and molecular physiology. 2008; 294(6):11149-57.
22. Babusyte A, Stravinskaite K., Jeroch J, Lotvall J, Sakalauskas R, Sitkauskiene B. Patterns of airway inflammation and MMP-12 expression in smokers and ex-smokers with COPD. Respir Res. 2007; 8:81. PMCID: PMC2200652.
23. Dalal S, Imai K, Mercer B, Okada Y, Chada K, D'Armiento J M. A role for collagenase (Matrix metalloproteinase-1) in pulmonary emphysema. Chest. 2000; 17(5 Suppl 1):227S-8S.
24. Shionil T, Okada Y, Foronjy R, Schiltz J, Jaenish R, Krane S, D'Armiento J. Emphysematous changes are caused by degradation of type III collagen in transgenic nice expressing MMP-1. Experimental lung research. 2003; 29(1):1-15.
25. Wallace A M, Loy L B, Abboud R T, D'Armiento J M, Coxson H O, Muller N L, Kalloger S, Li X, Mark Elliott W, English J C, Finley R J, Pare P D. Expression of Matrix Metalloproteinase-1 in Alveolar Macrophages, Type II Pneumocytes, and Airways in Smokers: Relationship to Lung Function and Emphysema. Lung. 2014.
26. Geraghty P, Dabo A J, D'Armiento J. TLR4 protein contributes to cigarette smoke-induced matrix metalloproteinase-1 (MMP-1) expression in chronic obstructive pulmonary disease. J Boil Chem. 2011; 286(34):30211-8. PMCID: PMC3191060.
27. D'Armiento J M, Goldklang M P, Hardigan A A, Geraghty P, Roth M D, Connett J R, Wise R A, Sciurba F C, Scharf S M, Thankachen J, Islam M, Ghio A J, Foronjy R F. Increased matrix metalloproteinase (MMPs) levels do not predict disease severity or progression in emphysema. PloS one. 2013; 8(2):e56352. PMCID: PMC3575373.
28. Hautamaki R D, Kobayashi D K, Senior R M, Shapiro S D. Requirement for macrophage elastase for cigarette smoke-induced emphysema in mice. Science. 1997; 277 (5334):2002-4.
29. Kochanek K D, Xu J, Murphy S L, Minino A M, Kung H. Deaths: preliminary data for 2009. Natl Vital Stat Rep. 2011; 59(4):1-50.
30. Mannino D M, Homa D M, Akinbami L J, Ford E S, Redd S C. Chronic obstructive pulmonary disease surveillance-United States, 1971-2000. Morbidity and mortality weekly report Surveillance summaries. 2002; 51(6): 1-16.

31. Mercer B A, Wallace A M, Brinckerhoff C E, D'Armiento J M. Identification of a cigarette smoke-responsive region in the distal MHP-1 promoter. American journal of respiratory cell and molecular biology. 2009; 40(1):4-12. PMCID: PMC2606945.
32. Yoshida T, Tuder R M. Pathobiology of cigarette smoke-induced chronic obstructive pulmonary disease. Physiological reviews. 2007; 87(3):1047-82.
33. Thomson E M, Williams A, Yauk C L, Vincent R. Overexpression of tumor necrosis factor-alpha in the lungs alters immune response, matrix remodeling, and repair and maintenance pathways. The American journal of pathology. 2012; 180(4):1413-30.
34. Letuve S, Kozhich A, Arouche N, Grandsaigne M, Reed J, Dombret M C, Kiener P A, Aubier M, Coyle A J, Pretolani M. YKL-40 is elevated in patients with chronic obstructive pulmonary disease and activates alveolar macrophages. J Immunol. 2008; 181(7):5167-73.
35. Karimi K, Sarir H, Mortaz E, Smit J J, Hosseini H, De Kimpe S J, Nijkamp F P, Folkerts G. Toll-like receptor-4 mediates cigarette smoke-induced cytokine production by human macrophages. Respir Res. 2006; 7:66. PMCID: PMC1481582.
36. Zheng T, Zhu Z, Wang Z, Homer R J, Ma B, Riese R J, Jr., Chapman H A, Jr., Shapiro S D, Elias J A. Inducible targeting of IL-13 to the adult lung causes matrix metalloproteinase- and cathepsin-dependent emphysema. The Journal of clinical investigation. 2000; 106(9):1081-93. PMCID: PMC301418.
37. Demedts I K, Morel-Montero A, Lehecpue S, Pacheco Y, Cataido D, Joos G E, Pauwels R A, Brusselle G G. Elevated MMP-12 protein levels in induced sputum from patients with COPD. Thorax. 2006; 61(3):196-201. PMCID: PMC2080750.
38. Sakao S, Tatsumi K, Hashimoto T, Igari H, Shino Y, Shirasawa H, Kuriyama T. Vascular endothelial growth factor and the risk of smoking-related COPD. Chest. 2003; 124(1):323-7.
39. Morissette M C, Parent J, Milot J. Alveolar epithelial and endothelial cell apoptosis in emphysema: what we know and what we need to know. Int J Chron Obstruct. Pulmon Dis. 2009; 4:19-31. PMCID: PMC2672789.
40. Martin T R, Nakamura H, Matute-Bello G. The role of apoptosis in acute lung injury. Critical care medicine. 2003; 31(4 Suppl):S184-8.
41. Herold S, Ludwig S, Pleschka S, Wolff T. Apoptosis signaling in influenza virus propagation, innate host defense, and lung injury. Journal of leukocyte biology. 2012; 92(1):75-82.
42. Drakopanagiotakis F, Xifteri A, Polychronopoulos V, Bouros D. Apoptosis in lung injury and fibrosis. The European respiratory journal. 2008; 32(6):1631-8.
43. Rottey S, Van den Bossche B, Slegers G, Van Belle S, van de Miele C. Influence of chemotherapy on the biodistribution of [99mTc]hydrazinonicotinamide annexin V in cancer patients. The quarterly journal of nuclear medicine and molecular imaging: official publication of the Italian Association of Nuclear Medicine. 2009; 53(2):127-32.
44. Kartachova M S, Valdes Olmos R A, Haas R L, Hoebers F J, van Herk M, Verheil M. 99mTc-HYNIC-rh-annexin-V scintigraphy: visual and quantitative evaluation of early treatment-induced apoptosis to predict treatment outcome. Nuclear medicine communications. 2008; 29(1):39-44,
45. Hoebers F J, Kartachova M, de Bois J, van den Brekel M W, van Tinteren H, van Herk M, Rasch C R, Valdes Olmos R A, Verheij M. 99mTc Hynic-rh-Annexin V scintigraphy for in vivo imaging of apoptosis in patients with head and neck cancer treated with chemoradiotherapy. European journal of nuclear medicine and molecular imaging. 2008; 35(3):509-18. PMCID: PMC2275773.
46. Loose D, Vermeersch H, De Vos F, Deron P, Siegers G, Van de Wiele C. Prognostic value of 99mTc-HYNIC annexin-V imaging in squamous cell carcinoma of the head and neck. European journal of nuclear medicine and molecular imaging. 2008; 35(1):47-52.
47. Pottey S, Slegers G, Van Belie S, Goethals I, Van de Miele C. Sequential 99mTc-hydrazinonicotinamide-annexin imaging for predicting response to chemotherapy. Journal of nuclear medicine: official publication, Society of Nuclear Medicine. 2006; 47(11):1813-8.
48. Lorberboym M, Blankenberg F G, Sadeh M, Lampl Y. In vivo imaging of apoptosis in patients with acute stroke: correlation with blood-brain barrier permeability. Brain research. 2006; 1103(1):13-9.
49. Blankenberg F G, Kalinyak J, Liu L, Koike M, Cheng D, Goris M L, Green A, Vanderheyden J L, Tong D C, Yenari M A. 99mTc-HYNIC-annexin V SPECT imaging of acute stroke and its response to neuroprotective therapy with anti-Fas ligand antibody. European journal of nuclear medicine and molecular imaging. 2006; 33(5):566-74.
50. Goldklang M P, Marks S M, D'Armiento J M. Second hand smoke and COPD: lessons from animal studies. Frontiers in physiology. 2013; 4:30. PMCID: PMC3583033.
51. Godier-Furnemont A F, Tekabe Y, Kollaros M, Eng G, Morales A, Vunjak-Novakovic G, Johnson L L. Noninvasive imaging of myocyte apoptosis following application of a stem cell-engineered delivery platform to acutely infarcted myocardium. Journal of nuclear medicine: official publication, Society of Nuclear Medicine. 2013; 54(6):977-83.
52. Johnson L L, Schofield L, Donahay T, Narula N, Narula J. 99mTC-annexin V imaging for in vivo detection of atherosclerotic lesions in porcine coronary arteries. Journal of nuclear medicine: official publication, Society of Nuclear Medicine. 2005; 46(7):1186-93.
53. Tekabe Y, Li Q, Luma J, Weisenberger D, Sedlar M, Harja B, Narula J, Johnson L L. Noninvasive monitoring the biology of atherosclerotic plaque development with radiolabeled annexin V and matrix metalloproteinase inhibitor in spontaneous atherosclerotic mice. Journal of nuclear cardiology: official publication of the American Society of Nuclear Cardiology. 2010; 17(6):1073-81.
54. Tait J F, Smith C, Blankenberg F G. Structural requirements for in vivo detection of cell death with 99mTc-annexin V. Journal of nuclear medicine: official publication, Society of Nuclear Medicine. 2005; 46(5):807-15. PMCID: PMC1201384.
55. Tait J F, Smith C, Levashova Z, Patel B, Blankenberg F G, Vanderheyden J L. Improved detection of cell death in vivo with annexin V radiolabeled by site-specific methods. Journal of nuclear medicine: official publication, Society of Nuclear Medicine. 2006; 47(9):1546-3.
56. Thomsen M, Ingebrigtsen T S, Marott J L, Dahl M, Lange P, Vestbo J, Nordestgaard B G. Inflammatory biomarkers and exacerbations in chronic obstructive pulmonary disease. Jama. 2013; 309(22):2353-61.
57. Wells J M, Washko G R, Han M K, Abbas N, Nath H, Mamary A J, Regan E, Bailey W C, Martinez F J, Westfall E, Beaty T H, Curran-Everett D, Curtis J L, Hokanson J E, Lynch D A, Make B J, Crapo J D, Silverman E K, Bowler R P, Dransfield M T, Investigators C O, Investigators E S. Pulmonary arterial enlargement and acute exacerbations of COPD. The New England journal of medicine. 2012; 367(10):913-21. PMCID: PMC3690810.
58. Kroenke K, Lawrence V A, Theroux J F, Tuley M R, Hilsenbeck S. Postoperative complications after thoracic and major abdominal surgery in patients with and without obstructive lung disease. Chest. 1993; 104(5):1445-51.
59. Gupta H, Ramanan B, Gupta P K, Fang X, Polich A, Modrykamien A, Schuller D, Morrow L E. Impact of COPD on postoperative outcomes: results from a national database. Chest. 2013; 143(6):1599-606.
60. Arozullah A M, Khuri S F, Henderson W G, Daley J, Participants in the National Veterans Affairs Surgical Quality Improvement P. Development and validation of a multifactorial risk index for predicting postoperative pneumonia after major noncardiac surgery. Annals of internal medicine. 2001; 135(10):847-57,
61. Thompson D A, Makary M A, Dorman T, Pronovost P J. Clinical and economic outcomes of hospital acquired pneumonia in intra-abdominal surgery patients, Annals of surgery. 2006; 243(4):547-52. PMCID: PMC1448956.
62. Lawrence V A, Hilsenbeck S G, Mulrow C D, Dhanda R, Sapp J, Page C P. Incidence and hospital stay for cardiac and pulmonary complications after abdominal surgery. Journal of general internal medicine. 1995; 10(12):671-8.
63. McAlister F A, Bertsch K, Man J, Bradley J, Jacka M. Incidence of and risk factors nor pulmonary complications after nonthoracic surgery. Am J Respir Crit Care Med. 2005; 171(5):514-7.
64. Halbertsma F J, Vaneker M, Scheffer G J, van der Hoeven J G. Cytokines and biotrauma in ventilator-induced lung injury: a critical review of the literature. The Netherlands journal of medicine. 2005; 63(10):382-92.
65. Hoegl S, Boost K A, Flondor M, Scheiermann P, Muhl H, Pfeilschifter J, Zwissier B, Hofstetter C. Short-term exposure to high-pressure ventilation leads to pulmonary biotrauma and systemic inflammation in the rat. International journal of molecular medicine. 2008; 21(4):513-9.
66. Imai Y, Kawano T, Miyasaka K, Takata. M, Imai T, Okuyama K. Inflammatory chemical mediators during conventional ventilation and during high frequency oscillatory ventilation. Am J Respir Crit Care Med. 1994; 150(6 Pt 1):1550-4.
67. Pugin J, Dunn I, Jolliet P, Tassaux D, Magnenat J L, Nicod L P, Chevrolet J C. Activation of human macrophages by mechanical ventilation in vitro. The American journal of physiology. 1998; 275(6 Pt 1):11040-50.
68. Imanaka H, Shimanka M, Matsuura N, Nishimura M, Ohta N, Kiyono H. Ventilator-induced lung injury is associated with neutrophil infiltration, macrophage activation, and TGF-beta. 1 mRNA upregulation. in rat lungs. Anesthesia and analgesia. 2001; 92(2):428-36.
69. Hammerschmidt S, Kuhn H, Grasenack T, Gessner C, Wirtz H. Apoptosis and necrosis induced by cyclic mechanical stretching in alveolar type II cells. American journal of respiratory cell and molecular biology. 2004; 30(3):396-402.
70. Syrkina O, Jafari B, Hales C A, Quinn D A. Oxidant stress mediates inflammation and apoptosis in ventilator-induced lung injury. Respirology. 2008; 13(3):333-40.
71. Futier E, Constantin J M, Paugam-Burtz C, Pascal J, Eurin M, Neuschwander A, Marret E, Beaussier M, Gutton C, Lefrant J Y, Allaouchiche M, Verzilli D, Leone M, De Jong A, Bazin C E, Pereira B, Jaber S, Group IS. A trial of intraoperative low-tidal-volume ventilation in abdominal surgery. The New England journal of medicine. 2013; 369(5):428-37.
72. Kor D J, Warner D O, Carter R E, Meade L A, Wilson G A, Li M. Hamersma M J, Hubmayr R D, Mauermann W J, Gajic O. Extravascular lung water and pulmonary vascular permeability index as markers predictive of postoperative acute respiratory distress syndrome: a prospective cohort investigation. Critical care medicine. 2015; 43(3):665-73.
73. Aschner Y, Zemans R L, Yamashita C M, Downey G P. Matrix metalloproteinases and protein tyrosine kinases: potential novel targets in acute lung injury and ARDS. Chest. 2014; 146(4):1081-91. PMCID: PMC4188143.
74. Uchida. T, Ito H, Yamamoto H, Ohno N, Asahara M, Yamada Y, Yamaguchi O, Tomita M, Makita K. Elevated levels of angiopoietin-2 as a biomarker for respiratory failure after cardiac surgery. Journal of cardiothoracic and vascular anesthesia. 2014; 28(5):1293-301.
75. Fernandez-Bustamante A, Klawitter J, Repine J E, Agazio A, Janocha A J, Shah C, Moss M, Douglas I S, Tran Z V, Erzurum S C, Christians U, Seres T. Early effect of tidal volume on lung injury biomarkers in surgical patients with healthy lungs. Anesthesiology. 2014; 121(3):469-81. PMCID: PMC4165799.
76. Binnie A, Tsang J L, dos Santos C C. Biomarkers in acute respiratory distress syndrome. Current opinion in critical care. 2014; 20(1):47-55.
77. Dickens J A, Miller B E, Edwards L D, Silverman E K, Lomas D A, Tal-Singer R, Evaluation of CLtISEsi. COPD association and repeatability of blood biomarkers in the ECLIPSE cohort. Respir Res. 2011; 12:146. PMCID: PMC3247194.
78. Johnson L L, Tekabe Y, Kollaros M, Eng G, Bhatia K, Li C, Krueger C G, Shanmuganayagam D, Schmidt A M. Imaging RAGE expression in atherosclerotic plaques in hyperlipidemic pigs. EJNMMI research. 2014; 4:26. PMCID: PMC4078320.
79. Guerra L, De Ponti E, Elisei F, Bettinardi V, Landoni C, Picchio M, Gilardi M C, Versari A, Fioroni F, Dziuk M Koza M, Ahond-Vionnet R, Collin B, Messa C. Respiratory gated. PET/CT in a European multicentre retrospective study: added diagnostic value in detection and characterization of lung lesions. European journal of nuclear medicine and molecular imaging. 2012; 39(9):1381-90.
80. Dey J, Segars W P, Pretorius P H, Walvick R P, Bruyant P P, Dahlberg S, King M A. Estimation and correction of cardiac respiratory motion in SPECT in the presence of limited-angle effects due to irregular respiration. Medical physics. 2010; 37(12):6453-65. PMCID: PMC3016095.
81. Iyer A S, Wells J M, Vishin S, Bhatt S P, Wille K M, Dransfield M T. CT scan-measured pulmonary artery to aorta ratio and echocardiography for detecting pulmonary hypertension in severe COPD. Chest. 2014; 145(4):824-32. PMCID: PMC3971971.
82. Lee E J, In K H, Kim J H, Lee S Y, Shin C, Shim J J, Kang K H, Yoo S H, Kim C H, Kim H K, Lee S H, Uhm C S. Proteomic analysis in lung tissue of smokers and COPD patients. Chest. 2009; 135(2):344-52.
83. Wagner S, Breyholz H J, Holtke C, Faust A, Schober O, Schafers M, Kopka K. A new 18F-labelled derivative of the MMP inhibitor CGS 27023A for PET: radiosynthesis and initial small-animal PET studies. Applied radiation and isotopes: including data, instrumentation and methods for use in agriculture, industry and medicine. 2009; 67(4): 606-10.

84. Wagner S, Breyholz H J, Faust A, Holtke C, Levkau B, Schober O, Schafers M, Kopka K. Molecular imaging of matrix metalloproteinases in vivo using small molecule inhibitors for SPECT and PET. Current medicinal chemistry. 2006; 13(23):2819-38.
85. Kopka K, Breyholz H J, Wagner S, Law M P, Riemann B, Schroer S, Trub M, Guilbert B, Levkau B, Schober O, Schafers M. Synthesis and preliminary biological evaluation of new radioiodinated MMP inhibitors for imaging MMP activity in vivo. Nuclear medicine and biology. 2004; 31(2):257-67.
86. Faust A, Waschkau B, Waldeck J, Holtke C, Breyholz H J, Wagner S, Kopka K, Schober O, Heindel W, Schafers M, Bremer C. Synthesis and evaluation of a novel hydroxamate based fluorescent photoprobe for imaging of matrix metalloproteinases. Bioconjugate chemistry. 2009; 20(5):904-12.
87. Romero-Perez D, Agrawal A, Jacobsen J, Yan Y, Thomas R, Cohen. S, Villarreal F. Effects of novel semiselective matrix metalloproteinase inhibitors on ex vivo cardiac structure-function. Journal of cardiovascular pharmacology. 2009; 53(6):452-61. PMCID: PMC2835692.
88. Ouchi H, Fujita M, Ikegame S, Ye Q, Inoshima I, Harada E, Kuwano K, Nakanishi Y. The role of collagenases in experimental pulmonary fibrosis. Pulmonary pharmacology & therapeutics. 2008; 21(2):401-8.
89. Rao V H, Meehan D T, Delimont D, Nakajima M, Wada T, Gratton M A, Cosgrove D. Role for macrophage metalloelastase in glomerular basement membrane damage associated with alport syndrome. The American journal of pathology. 2006; 169(1):32-46. PMCID: PMC1698763.
90. Behrends M, Wagner S, Kopka K, Schober O, Schafers M, Kumbhar S, Waller M, Haufe G. New matrix metalloproteinase inhibitors based on gamma-fluorinated alpha-aminocarboxylic and alpha-aminohydroxamic acids. Bioorganic & medicinal chemistry. 2015; 2(13): 3809-18.
91. Markwell M A, Fox C F. Surface-specific iodination of membrane proteins of viruses and eucaryotic cells using 1,3,4,6-tetrachloro-3alpha,6alpha-diphenyiglycoluril. Biochemistry. 1978; 17(22):4807-17.
92. Carver P I, Anguiano V, D'Armiento J M, Shiomi T. Mmp1a and Mmp1b are not functional orthologs to human MMP1 in cigarette smoke induced lung disease. Experimental and toxicologic pathology: official journal of the Gesellschaft fur Toxikologische Pathologie, 2015; 67(2):153-9. PMCID: PMC4308467.
93. Mehra D, Sternberg D I, Jia Y, Canfield S., Lemaitre V, Nkyimbeng T, Wilder J, Sonett J, D'Armiento J. Altered lymphocyte trafficking and diminished airway reactivity in transgenic mice expressing human MNP-9 in a mouse model of asthma. American journal of physiology Lung cellular and molecular physiology. 2010; 298(2):L189-96. PMCID: PMC2822563.
94. Wedzicha J A, Brill S E, Allinson J P, Donaldson G C. Mechanisms and impact of the frequent exacerbator phenotype in chronic obstructive pulmonary disease. BMC medicine. 2013; 11:181, PMCID: PMC3750926.
95. Donaldson G C, Seemungal T A, Bhowmik A, Wedzicha J A. Relationship between exacerbation frequency and lung function decline in chronic obstructive pulmonary disease. Thorax. 2002; 57(10):847-52. PMCID: PMC1746193.
96. Gelbert L M, Wilson M M, Davidson R L. Analysis of GPT activity in mammalian cells with a chromosomally integrated shuttle vector containing altered gpt genes. Somatic cell and molecular genetics. 1990; 16(2):173-84.
97. Karg M J, Lee C G, Lee J Y, Dela Cruz C S, Chen Z J, Enelow R, Elias J A. Cigarette smoke selectively enhances viral PAMP- and virus-induced pulmonary innate immune and remodeling responses in mice. The Journal of clinical investigation. 2008; 118(8):2771-84. PMCID: PMC2483678,
98. Takaishi H, Kimura T, Dalai S, Okada Y, D'Armiento J. Joint. diseases and matrix metalloproteinases: a role for MMP-13. Current pharmaceutical biotechnology. 2008; 9(1):47-54.

What is claimed is:

1. A method of imaging a subject's lung which comprises administering to the subject an amount of a matrix metalloproteinase inhibitor labeled with an I-123 or F-18 radioisotope under conditions such that the inhibitor binds to matrix metalloproteinase in the lung, and then imaging the radiolabeled inhibitor bound to matrix metalloproteinase in the subject's lung so as to image the subject's lung, wherein the matrix metalloproteinase inhibitor is Ro 32-3555 which has the following formula

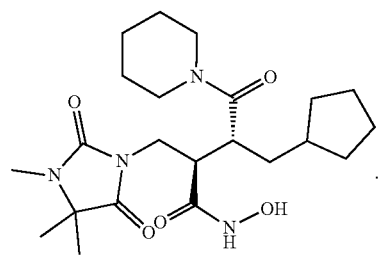 [SMILES: CN1C(=O)N(C[C@H](C(=O)NO)[C@@H](CC2CCCC2)C(=O)N2CCCCC2)C(=O)C1(C)C]

2. The method of claim 1, wherein the radioisotope is 1-123.
3. Ro 32-3555 labeled with an 1-123 or F-18 radioisotope.
4. The labeled Ro 32-3555 of claim 3 wherein the radioisotope is 1-123.

* * * * *